United States Patent
Schnabel et al.

(10) Patent No.: US 7,163,910 B1
(45) Date of Patent: Jan. 16, 2007

(54) FORMULATION OF HERBICIDES AND PLANT GROWTH REGULATORS

(75) Inventors: Gerhard Schnabel, Elsenfeld (DE); Detlev Haase, Frankfurt (DE); Thomas Maier, Hofheim (DE); Julio Martinez de Una, Liederbach (DE); Jochen Würtz, Bingen am Rhein (DE)

(73) Assignee: Bayer CropScience GmbH, Frankfurt am Main (DE)

( * ) Notice: Subject to any disclaimer, the term of this patent is extended or adjusted under 35 U.S.C. 154(b) by 0 days.

(21) Appl. No.: 09/890,086

(22) PCT Filed: Jan. 22, 2000

(86) PCT No.: PCT/EP00/00469

§ 371 (c)(1),
(2), (4) Date: Nov. 26, 2001

(87) PCT Pub. No.: WO00/44227

PCT Pub. Date: Aug. 3, 2000

(30) Foreign Application Priority Data

Dec. 28, 1999 (DE) .................................. 199 63 383

(51) Int. Cl.
*A01N 47/36* (2006.01)
*A01P 13/00* (2006.01)

(52) U.S. Cl. ...................... 504/212; 504/214
(58) Field of Classification Search ................ 504/212; 544/213
See application file for complete search history.

(56) References Cited

U.S. PATENT DOCUMENTS

| 3,942,973 | A | 3/1976 | Wittenbrook et al. ......... 71/103 |
|---|---|---|---|
| 4,106,747 | A | 8/1978 | Malacheski et al. ......... 251/84 |
| 4,173,463 | A | 11/1979 | Peterson et al. ............. 71/87 |
| 4,191,553 | A | 3/1980 | Reap ............................ 71/92 |
| 4,629,810 | A | 12/1986 | Meyer et al. ................ 564/89 |
| 4,806,682 | A | 2/1989 | Yih ............................ 562/474 |
| 5,104,443 | A | 4/1992 | Kehne et al. .................. 71/92 |
| 5,188,657 | A | 2/1993 | Hamprecht et al. ......... 504/212 |
| 5,369,083 | A | 11/1994 | Schurter et al. ........... 504/215 |
| 5,696,053 | A | 12/1997 | Schnabel et al. ........... 504/214 |
| 5,773,387 | A | 6/1998 | Sorokin ..................... 504/134 |
| 6,413,911 | B1 * | 7/2002 | Mayer et al. ............... 504/214 |
| 6,451,737 | B1 * | 9/2002 | Gesing et al. ............. 504/212 |

FOREIGN PATENT DOCUMENTS

| CA | 2005595 | 7/1990 |
|---|---|---|
| CA | 2036334 | 8/1992 |
| CA | 2073135 | 1/1993 |
| DE | 196 16 362 | 10/1997 |
| EP | 0 052 856 | 6/1982 |
| WO | 96/41537 | * 12/1996 |
| WO | WO 97/32875 | 9/1997 |
| WO | WO 97/40021 | 10/1997 |
| WO | WO 98/21963 | 5/1998 |

* cited by examiner

*Primary Examiner*—S. Mark Clardy
(74) *Attorney, Agent, or Firm*—Frommer Lawrence & Haug LLP

(57) ABSTRACT

The present invention relates to formulations comprising
a) at least one phosphonium or sulfonium salt of a sulfonylurea, where the phosphonium and sulfonium cation of the salt has at least one substituent which is different from hydrogen, and
b) customary auxiliaries and additives.

25 Claims, No Drawings

FORMULATION OF HERBICIDES AND PLANT GROWTH REGULATORS

The invention relates to the technical field of the formulation of herbicides and plant growth regulators, in particular of herbicides for controlling undesirable vegetation, for example of broad-leaved weeds and weed grasses in crops of useful plants.

It is known that sulfonylureas have herbicidal and plant-growth-regulating properties. For use in agrochemistry, it is customary to formulate the sulfonylureas. Here, the chemical stability and the concentration of the active compound in the formulation are important for their activity.

Surprisingly, it has now been found that formulations based on certain sulfonylurea salts have excellent properties.

Accordingly, the present invention provides formulations, in particular agrochemical, for example herbicidal, formulations, comprising a) at least one phosphonium or sulfonium salt of a sulfonylurea, where the phosphonium and sulfonium cation of the salt has at least one substituent which is different from hydrogen, and b) customary auxiliaries and additives.

In a preferred embodiment, the present invention relates to formulations, in particular emulsifiable concentrates (EC), comprising at least one primary, secondary, tertiary or quaternary, preferably a quaternary, phosphonium salt or at least one primary, secondary or tertiary, preferably a tertiary, sulfonium salt of a sulfonylurea.

Preference is given to formulations comprising a sulfonylurea salt of the formula (Ia),

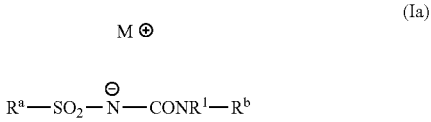
(Ia)

in which $R^a$ is a substituted aliphatic, aromatic or heterocyclic radical or an electron-withdrawing group, such as a substituted sulfonamide radical;

preferably $R^a$ is a radical of the formula II–IVc,

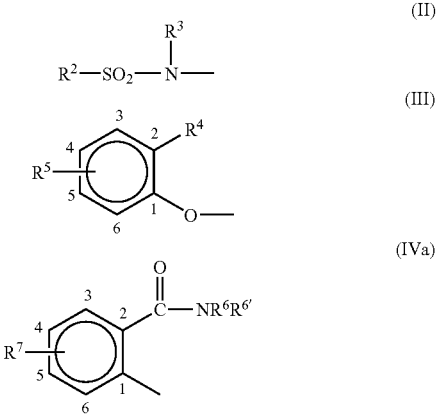

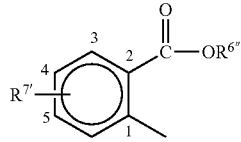
(IVb)

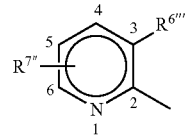
(IVc)

$R^b$ is a heterocyclyl radical, preferably a nitrogen-containing heterocyclyl radical, particularly preferably a heterocyclyl radical having 2 or 3 nitrogen atoms in the ring, very particularly preferably a radical

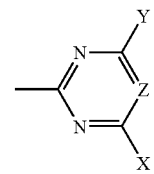

in which $R^1$ is H or a $C_1$–$C_{10}$-hydrocarbon radical, such as ($C_1$–$C_6$)-alkyl, $R^2$ is a substituted or unsubstituted $C_1$–$C_{20}$-hydrocarbon radical, such as substituted or unsubstituted ($C_1$–$C_6$)-alkyl, substituted or unsubstituted ($C_2$–$C_6$)-alkenyl, substituted or unsubstituted ($C_2$–$C_6$)-alkynyl, substituted or unsubstituted ($C_3$–$C_7$)-cycloalkyl, $R^3$ is a substituted or unsubstituted $C_1$–$C_{20}$-hydrocarbon radical, such as substituted or unsubstituted ($C_1$–$C_6$)-alkyl, substituted or unsubstituted ($C_2$–$C_6$)-alkenyl, substituted or unsubstituted ($C_2$–$C_6$)-alkynyl, substituted or unsubstituted ($C_3$–$C_7$)-cycloalkyl, $R^4$ is halogen, such as F, Cl, Br, I, or a substituted or unsubstituted $C_1$–$C_{20}$-hydrocarbon radical or $C_1$–$C_{20}$-hydrocarbonoxy radical, such as ($C_1$–$C_6$)-alkyl, ($C_2$–$C_6$)-alkenyl, ($C_2$–$C_6$)-alkynyl, ($C_1$–$C_6$)-alkoxy, ($C_3$–$C_6$)-alkenyloxy, ($C_3$–$C_6$)-alkynyloxy, where the 6 last-mentioned radicals may be substituted by one or more radicals, preferably from the group consisting of halogen, such as F, Cl, Br or I, and ($C_1$–$C_3$)-alkoxy, $R^5$ is H, halogen, such as F, Cl, Br, I, or a substituted or unsubstituted $C_1$–$C_{20}$-hydrocarbon radical or $C_1$–$C_{20}$-hydrocarbonoxy radical, such as ($C_1$–$C_6$)-alkyl, which may be substituted by one or more radicals from the group consisting of halogen, such as F, Cl, Br or I, and ($C_1$–$C_3$)-alkoxy, or ($C_1$–$C_5$)-alkoxy which may be substituted by one or more radicals from the group consisting of halogen (F, Cl, Br, I) and ($C_1$–$C_3$)-alkoxy, $R^6$ and $R^{6'}$ are identical or different and are H or a substituted or unsubstituted $C_1$–$C_{20}$-hydrocarbon radical, such as $C_1$–$C_6$-alkyl (for example Me, Et, $^n$Pr, $^i$Pr, $^c$Pr), where $R^6$ and $R^{6'}$ may form an unsubstituted or substituted ring, $R^7$ is H, halogen, such as F, Cl, Br or I, OH, $NR^xR^y$, in which $R^x$ and $R^y$ are H or $(C_1-C_3)$-alkyl, or $R^7$ is $N-(C_1-C_3)$-alkyl-N-acylamino, N-acylamino or a substituted or unsubstituted $C_1-C_{20}$-hydrocarbon radical or hydrocarbonoxy radical, such as $(C_1-C_3)$-alkyl, $(C_1-C_3)$-haloalkyl, halogen, $(C_1-C_3)$-alkyl-$(N-(C_1-C_3)$-alkyl-N-acylamino), $(C_1-C_3)$-alkyl-(N-acylamino) or $(C_1-C_3)$-alkoxy, $R^{6''}$ is a substituted or unsubstituted $C_1-C_{20}$-hydrocarbon radical, such as substituted or unsubstituted $(C_1-C_6)$-alkyl, substituted or unsubstituted $(C_3-C_6)$-alkenyl, substituted or unsubstituted $(C_3-C_6)$-cycloalkyl, substituted or unsubstituted $(C_3-C_7)$-alkynyl, substituted or unsubstituted $(C_4-C_8)$-cycloalkylalkyl, $R^{7'}$ is halogen, such as F, Cl, Br or I, OH, $NR^xR^y$, in which $R^x$ and $R^y$ are H or $(C_1-C_3)$-alkyl, or $R^{7'}$ is $N-(C_1-C_3)$-alkyl-N-acylamino, N-acylamino or a substituted or unsubstituted $C_1-C_{20}$-hydrocarbon radical or $C_1-C_{20}$-hydrocarbonoxy radical, such as $(C_1-C_3)$-alkyl, $(C_1-C_3)$-haloalkyl, $(C_1-C_3)$-alkyl-$(N-(C_1-C_3)$-alkyl-N-acylamino), $(C_1-C_3)$-alkyl-(N-acylamino) or $(C_1-C_3)$-alkoxy, $R^{6'''}$ is halogen, such as F, Cl, Br or I, or a substituted or unsubstituted $C_1-C_{20}$-hydrocarbon-containing radical, such as $(C_1-C_6)$-alkyl, which may be substituted by one or more radicals from the group consisting of halogen (F, Cl, Br, I) and $(C_1-C_3)$-alkoxy, $(C_1-C_6)$-alkoxy which may be substituted by one or more radicals from the group consisting of halogen (F, Cl, Br, I) or $(C_1-C_3)$-alkoxy, substituted or unsubstituted alkoxycarbonyl, substituted or unsubstituted dialkylamino carbonyl, substituted or unsubstituted $(C_1-C_6)$-alkylsulfonyl $(C_1-C_6)$-mono- or -dialkylamino, $N-(C_1-C_6)$-alkyl-N-acylamino or N-acylamino, $R^{7''}$ is halogen, such as F, Cl, Br or I, OH, $NR^xR^y$, in which $R^x$ and $R^y$ are H or $(C_1-C_3)$-alkyl, or $R^{7''}$ is a substituted or unsubstituted $C_1-C_{20}$-hydrocarbon radical or hydrocarbonoxy radical, such as $(C_1-C_6)$-alkyl, $(C_1-C_6)$-haloalkyl, $(C_1-C_6)$-alkoxy or $(C_1-C_6)$-haloalkoxy, $M^+$ is a quaternary phosphonium ion or a tertiary sulfonium ion, X is substituted or unsubstituted $(C_1-C_6)$-alkyl, substituted or unsubstituted $(C_1-C_6)$-alkoxy, halogen, such as F, Cl, Br or I, substituted or unsubstituted $(C_1-C_6)$-mercaptoalkyl or $(C_1-C_3)$-mono- or $(C_1-C_3)$-dialkylamino, Y is substituted or unsubstituted $(C_1-C_6)$-alkyl, substituted or unsubstituted $(C_1-C_6)$-alkoxy, halogen, such as F, Cl, Br or I, substituted or unsubstituted $(C_1-C_6)$-mercaptoalkyl or $(C_1-C_3)$-mono- or $(C_1-C_3)$-dialkylamino, and Z is C-halogen, such as CF, CCl, CBr or Cl, CH or N.

The sulfonylurea salts of the formula (Ia) are novel and likewise form part of the subject matter of this invention.

In the formula (Ia) and in the other formulae used in this application, the radicals alkyl, alkoxy, haloalkyl, haloalkoxy, alkylamino and alkylthio and the corresponding unsaturated and/or substituted radicals can in each case be straight-chain or branched in the carbon skeleton. Alkyl radicals, including in the composite meanings such as alkoxy, haloalkyl, etc., are, for example, methyl, ethyl, n- or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

The abbreviations used in this application have the following meanings: Me=methyl, Et=ethyl, Pr=propyl, Bu=butyl, $^n$Pr=n-propyl, $^i$Pr=isopropyl, $^c$Pr=cyclopropyl, $^n$Bu=n-butyl, $^i$Bu=isobutyl, $^s$Bu=secondary butyl, $^t$Bu=tertiary butyl, $^c$Bu=cyclobutyl, Ph=phenyl.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic and unsubstituted or substituted; it preferably contains one or more heteroatoms in the ring, preferably selected from the group consisting of N, O and S; it is preferably an aliphatic heterocyclyl radical having 3 to 7 ring atoms or a heteroaromatic radical having 5 to 6 ring atoms and contains 1, 2 or 3 heteroatoms. The heterocyclic radical can, for example, be a heteroaromatic radical or ring (heteroaryl), such as, for example, a mono-, bi- or polycyclic aromatic ring system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical, such has oxiranyl, oxetanyl, pyrrolidyl, piperidyl, piperazinyl, dioxolanyl, morpholinyl, tetrahydrofuryl. Suitable substituents for a substituted heterocyclic radical are the substituents mentioned further below, and additionally also oxo. The oxo group can also be present at the heteroring atoms which can exist in different oxidation states, for example in the case of nitrogen and sulfur.

Substituted radicals, such as substituted hydrocarbon radicals, for example substituted alkyl, alkenyl, alkynyl, aryl, phenyl and benzyl, or substituted heteroaryl, a substituted bicyclic radical or ring or a substituted bicyclic radical, if appropriate with aromatic moieties, are, for example, substituted radicals which are derived from the unsubstituted parent compounds, where the substituents are, for example, one or more, preferably 1, 2 or 3, radicals selected from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and also unsaturated aliphatic radicals which correspond to the saturated hydrocarbon-containing radicals mentioned, such as alkenyl, alkynyl, alkenyloxy, alkynyloxy, etc. In the case of radicals having carbon atoms, preference is given to those having 1 to 4 carbon atoms, in particular 1 or 2 carbon atoms.

Mono- and disubstituted amino is, for example, alkylamino, dialkylamino, acylamino, arylamino, N-aryl-N-alkylamino.

An acyl radical is the radical of an organic acid, for example the radical of a carboxylic acid and radicals of acids derived therefrom, such as thiocarboxylic acid, optionally N-substituted iminocarboxylic acids, or the radical of carbonic monoesters, optionally N-substituted carbamic acid, sulfonic acids, sulfinic acids, phosphonic acids, phosphinic acids. Acyl is, for example, formyl, alkylcarbonyl, such as ($C_1$–$C_4$-alkyl)carbonyl, phenylcarbonyl, where the phenyl ring may be substituted, for example as indicated above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The formula (Ia) also embraces all stereoisomers of the formula (Ia), and mixtures thereof. Such compounds of formula (Ia) contain one or more asymmetric carbon atoms or else double bonds, which are not indicated separately in the general formula (Ia). The possible stereoisomers defined by their specific spatial form, such as enantiomers, diastereomers and Z and E isomers, are all embraced by the formulae (Ia) and can be obtained by conventional methods from mixtures of these stereoisomers or else can be prepared by stereoselective reactions in combination with the use of stereochemically pure starting materials.

Of particular interest are formulations comprising sulfonylurea salts of the formula (Ia) in which $R^1$ is H or Me, $R^2$ is ($C_1$–$C_3$)-alkyl or ($C_1$–$C_3$)-haloalkyl, in particular Me and Et, $R^3$ is ($C_1$–$C_3$)-alkyl or ($C_1$–$C_3$)-haloalkyl, in particular Me and Et, $R^4$ is ($C_1$–$C_6$)-alkyl or ($C_1$–$C_6$)-haloalkyl or ($C_1$–$C_6$)-alkoxy, in particular Me, Et, OMe, OEt or $CF_3$, $R^5$ is H, halogen, such as F, Cl, Br or I, OMe, OEt, Me, $CF_3$, where the radicals $R^5$ in the formula (III) which are different from hydrogen are preferably located in the 5-position on the phenyl ring, $R^6$ and $R^{6'}$ are identical or different $C_1$–$C_6$-alkyl radicals, preferably $R^6$=Me, $R^{6'}$=Me; $R^6$=Me, $R^{6'}$=Et and $R^{6'}$=Et, $R^6$=Et, $R^7$ is H, Me, Et, $CF_3$, F, Cl, Br, I, N[($C_1$–$C_3$)-alkyl]-$R^8$, NH—$R^9$, $CH_2$N[($C_1$–$C_3$)-alkyl]-$R^{10}$, $CH_2$NH—$R^{11}$, $CH_2CH_2$N[($C_1$–$C_3$)-alkyl]-$R^{12}$, $CH_2CH_2$NH—$R^{13}$, where the radicals $R^7$ in the formula (IVa) which are different from hydrogen are preferably located in the 5-position on the phenyl ring and the radicals $R^8$ to $R^{13}$ are H, ($C_1$–$C_6$)-alkyl, ($C_1$–$C_6$)-haloalkyl, CHO, COO($C_1$–$C_6$)-alkyl, COO ($C_1$–$C_6$)-haloalkyl, $SO_2$—($C_1$–$C_6$)-alkyl or $SO_2$—($C_1$–$C_6$)-haloalkyl, CO—($C_1$–$C_6$)-alkyl or CO—($C_1$–$C_6$)-haloalkyl, $R^{6''}$ is Me, Et, $^n$Pr, $^i$Pr, $^c$Pr, $^n$Bu, $^i$Bu, $^s$Bu, $^t$Bu, $^c$Bu, in particular Me or Et, $R^{7'}$ is H, Me, Et, $CF_3$, F, Cl, Br, I, N[($C_1$–$C_3$)-alkyl]-$R^8$, NH—($C_1$–$C_3$)-alkyl, $CH_2$N[($C_1$–$C_3$)-alkyl]-$R^{10}$, $CH_2$NH—$R^{11}$, $CH_2CH_2$N[($C_1$–$C_3$)-alkyl]-$R^{12}$, $CH_2CH_2$NH—$R^{13}$, where the radicals $R^{7'}$ in the formula (IVb) which are different from hydrogen are preferably located in the 5-position on the phenyl ring and the radicals $R^8$ and $R^{10}$ to $R^{13}$ are H, ($C_1$–$C_6$)-alkyl, ($C_1$–$C_6$)-haloalkyl, CHO, COO ($C_1$–$C_6$)-alkyl, COO($C_1$–$C_6$)-haloalkyl, $SO_2$—($C_1$–$C_6$)-alkyl, $SO_2$—($C_1$–$C_6$)-haloalkyl, CO—($C_1$–$C_6$)-alkyl or CO—($C_1$–$C_6$)-haloalkyl, $R^{6'''}$ is Me, Et, Pr, $CH_2CH_2CF_3$, OMe, OEt, $O^i$Pr, $OCH_2CH_2$Cl, F, Cl, COOMe, COOEt, $COO^n$Pr, $COO^i$Pr, $CONMe_2$, $CONEt_2$, $SO_2$Me, $SO_2$Et, $SO_2^i$Pr, unsubstituted or substituted NH—($C_1$–$C_6$)-alkyl-acyl, unsubstituted or substituted NH—($C^3$–$C_7$)-cycloalkyl, unsubstituted or substituted ($C_4$–$C_8$)-cycloalkylalkyl, unsubstituted or substituted N—($C_3$–$C_7$)-cycloalkyl-aryl, unsubstituted or substituted N—($C_4$–$C_8$)-cycloalkylalkyl-acyl, preferably N—($C_1$–$C_6$)-alkyl-CHO, N—($C_1$–$C_6$)-alkyl-CO—R, N—($C_1$–$C_6$)-alkyl-$SO_2$R, NH—CHO, NH—CO—R, $NHSO_2$R, where the radicals R are ($C_1$–$C_6$)-(halo)alkyl, ($C_1$–$C_6$)-(halo)alkoxy, ($C_1$–$C_3$)-alkoxy-($C_1$–$C_6$)-alkyl, ($C_1$–$C_3$)-alkoxy-($C_1$–$C_6$)-alkoxy or mono- and di-($C_1$–$C_6$)-alkylamino, $R^{7'''}$ is H, F, Cl, Me, Et, $CF_3$, $OCH_3$, OEt, $OCH_2CF_3$, preferably H, $M^+$ is $[SR^{18}R^{19}R^{20}]^+$ or $[PR^{21}R^{22}R^{23}R^{24}]^+$, where $R^{18}$ to $R^{25}$ are identical or different from one another and are substituted or unsubstituted ($C_1$–$C_{30}$)-alkyl, substituted or unsubstituted ($C_1$–$C_{10}$)-alkyl-(hetero)aryl, substituted or unsubstituted ($C_3$–$C_{30}$)-(oligo)alkenyl, substituted or unsubstituted ($C_3$–$C_{10}$)-(oligo)alkenyl-(hetero)aryl, substituted or unsubstituted ($C_3$–$C_{30}$)-(oligo)alkynyl, substituted or unsubstituted ($C_3$–$C_{10}$)-(oligo)alkynyl-(hetero)aryl, substituted or unsubstituted (hetero)aryl and where two radicals $R^{18}/R^{19}$, $R^{21}/R^{22}$ and $R^{23}/R^{24}$ together may form an unsubstituted or substituted ring, X is Me, Et, Pr, $^i$Pr, $CF_3$, $CCl_3$, OMe, OEt, $O^i$Pr, $OCHCl_2$, $OCH_2CCl_3$, $OCH_2CF_3$, F, Cl, Br, SMe, SEt, NHMe, $NMe_2$, NHEt, preferably OMe, OEt, Me, Cl Y is Me, Et, Pr, $^i$Pr, $CF_3$, $CCl_3$, OMe, OEt, $O^i$Pr, $OCHCl_2$, $OCH_2CCl_3$, $OCH_2CF_3$, F, Cl, Br, SMe, SEt, NHMe, $NMe_2$, NHEt, preferably OMe, OEt, Me, Cl and Z is CH or N.

Suitable cations $M^+$ include cyclic cations of the formula $$[SR^{18}R^{19}R^{20}]^+ \text{ or } [PR^{21}R^{22}R^{23}R^{24}]^+,$$

in which two radicals $R^{18}/R^{19}$, $R^{21}/R^{22}$ or $R^{23}/R^{24}$ together form an unsubstituted or substituted ring.

$R^{18}/R^{19}$ together with the charge-bearing sulfur atom can, for example, form a heterocyclic ring, such as, for example, shown in formulae X–XII

(X)

(XI)

(XII)

or

R$^{21}$/R$^{22}$ together with the charge-bearing phosphorus atom form a heterocyclic ring, such as, for example, shown in formulae Xa–XIIa

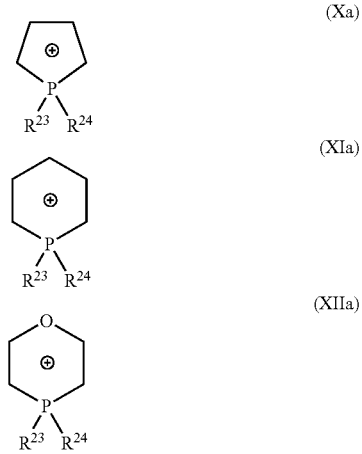

Particular preference is given to cations M$^+$ in which

R$^{18}$ to R$^{24}$ are identical or different from one another and are (C$_1$–C$_{22}$)-alkyl, unsubstituted or substituted by one or more radicals selected from the group consisting of (C$_1$–C$_5$)-alkyl, (C$_1$–C$_5$)-alkoxy, (C$_1$–C$_5$)-haloalkoxy, halogen, such as fluorine, chlorine, bromine and iodine, O—(CH$_2$—CH$_2$—O)$_x$H, O—(CH$_2$—CH$_2$—O)$_x$—(C$_1$–C$_3$)-alkyl, O—(CH$_2$—CH$_2$—O)$_x$—(CO)—(C$_1$–C$_3$)-alkyl or O—(CH$_2$—CH$_2$—O)$_x$—(CO)—(C$_1$–C$_3$)-alkoxy, phenyl, unsubstituted or substituted by one or more radicals selected from the group consisting of (C$_1$–C$_5$)-alkyl, (C$_1$–C$_5$)-alkoxy, (C$_1$–C$_5$)-haloalkoxy, halogen, such as fluorine, chlorine, bromine and iodine, O—(CH$_2$—CH$_2$—O)$_x$H, O—(CH$_2$—CH$_2$—O)$_x$—(C$_1$–C$_3$)-alkyl, O—(CH$_2$—CH$_2$—O)$_x$—(CO)—(C$_1$–C$_3$)-alkyl, O—(CH$_2$—CH$_2$—O)$_x$(CO)—(C$_1$–C$_3$)-alkoxy, C$_1$–C$_{10}$-alkyl, which may likewise be substituted by one of the radicals O—(CH$_2$—CH$_2$)$_x$—OH, O—(CH$_2$—CH$_2$)$_x$—O—(C$_1$–C$_3$)-alkyl, O—(CH$_2$—CH$_2$—O)X—(CO)—(C$_1$–C$_3$)-alkyl or O—(CH$_2$—CH$_2$—O)$_x$—(CO)—(C$_1$–C$_3$)-alkoxy, (C$_3$–C$_{22}$)-alkenyl, unsubstituted or substituted by one or more radicals selected from the group consisting of (C$_1$–C$_5$)-alkyl, (C$_1$–C$_5$)-alkoxy, (C$_1$–C$_5$)-haloalkoxy, halogen, such as fluorine, chlorine, bromine and iodine, O—(CH$_2$—CH$_2$—O)$_x$H, O—(CH$_2$—CH$_2$—O)$_x$—(C$_1$–C$_3$)-alkyl, O—(CH$_2$—CH$_2$—O)$_x$—(CO)—(C$_1$–C$_3$)-alkyl or O—(CH$_2$—CH$_2$—O)$_x$—(CO)—(C$_1$–C$_3$)-alkoxy, where the alkenyl radical is mono- or polyunsaturated and preferably carries from one to three double bonds, (C$_3$–C$_{22}$)-alkynyl, unsubstituted or substituted by one or more radicals selected from the group consisting of (C$_1$–C$_5$)-alkyl, (C$_1$–C$_5$)-alkoxy, (C$_1$–C$_5$)-haloalkoxy, halogen, such as fluorine, chlorine, bromine and iodine, O—(CH$_2$—CH$_2$—O)$_x$H, O—(CH$_2$—CH$_2$—O)$_x$—(C$_1$–C$_3$)-alkyl, O—(CH$_2$—CH$_2$)$_x$—(CO)—(C$_1$–C$_3$)-alkyl or O—(CH$_2$—CH$_2$—O)$_x$—(CO)—(C$_1$–C$_3$)-alkoxy, where the alkynyl radical is mono- or polyunsaturated, and preferably carries from one to three triple bonds, where x is an integer of from 1 to 40.

The abovementioned sulfonylurea salts, preferably those of the formula (Ia), in combination with auxiliaries and additives, are suitable for preparing formulations, in particular for preparing EC formulations.

The following are examples of possible formulations: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

Formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" [Surface-active ethylene oxide adducts], Wiss. Verlagsgesell., Stuttgart 1976;

Winnacker-Küchler, "Chemische Technologie" [Chemical Technology], Volume 7, C. HauserVerlag Munich, 4th Ed. 1986.

Based on these formulations, it is also possible to prepare combinations with other pesticidally active substances, such as, for example, insecticides, acaricides, herbicides, fungicides, and also with safeners, such as ethyl 1-(2,4-dichlorophenyl)-5-(ethoxycarbonyl)-5-methyl-2-pyrazoline-3-carboxylate (Mefenpyr) or ethyl 5,5-diphenyl-2-isoxazoline-carboxylate, fertilizers and/or growth regulators, for example in the form of a ready mix or a tank mix.

Wettable powders are preparations which are uniformly dispersible in water and which, besides the active substance, also comprise ionic and/or nonionic surfactants (wetting agents, dispersants), for example poly-ethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthyl-methane-6,6'-disulfonate, sodium dibutylnaphthalenesulfonate or else sodium oleoylmethyltaurinate, in addition to a diluent or inert substance. To prepare the wettable powders, the herbicidally active substances are ground finely, for example in customary equipment such as hammer mills, blower mills and air-jet mills, and simultaneously or subsequently mixed with the formulation auxiliaries.

Emulsifiable concentrates are prepared, for example, by dissolving the active substance in an organic solvent, for example butanol, cyclo-hexanone, dimethylformamide, xylene, or else higher-boiling aromatics or hydrocarbons or mixtures of the organic solvents with the addition of one or more ionic and/or nonionic surfactants (emulsifiers). Examples of emulsifiers which can be used are: calcium salts of alkylarylsulfonic acids such as calcium dodecylbenzenesulfonate, or nonionic emulsifiers such as alkylaryl polyglycol ethers which are different than para-alkyl phenol ethoxylates, fatty acid polyglycol esters, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet grinding using commercially available bead mills with an optional addition of surfactants such as have already been mentioned above for example in the case of the other types of formulation.

Emulsions, for example oil-in-water emulsions (EW), can be prepared for example by means of stirrers, colloid mills and/or static mixers using aqueous organic solvents and, if appropriate, surfactants such as have already been mentioned above for example in the case of the other types of formulation.

Granules can be prepared either by spraying the active substance onto adsorptive granulated inert material or by applying active substance concentrates to the surface of carriers such as sand, kaolinites or of granulated inert material by means of binders, for example sugar and pentoses and hexoses or else mineral oils. Suitable active substances can also be granulated in the manner which is conventional for the production of fertilizer granules, if desired as a mixture with fertilizers.

Water-dispersible granules are generally prepared by the customary processes such as spray drying, fluidized-bed granulation, disk granulation, mixing with high-speed mixers and extrusion without solid inert material.

For the preparation of disk, fluidized-bed, extruder and spray granules, see, for example, the processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

In addition, the abovementioned formulations of active substances comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Novel and also part of the subject matter of this invention is the use of the auxiliaries of the formula (XVIII) as formulation auxiliaries for agrochemical formulations and their use in the synthesis of salts of agrochemically active compounds having acidic proton(s).

$$R\text{---}O(EO)_w(PO)_x(EO)_y(PO)_z{}^{\ominus}M^{\oplus} \quad \text{(XVIII)}$$

The auxiliaries of the formula (XVIII) can be used as a pure substance or in the form of a solid or liquid mixture. In the formula (XVIII), the indices w, x, y and z can, independently of one another, be an integer of from 0 to 50, preferably from 0 to 20, particularly preferably from 1 to 20. The radical R is an unsubstituted or substituted $C_8$–$C_{40}$-hydrocarbon radical, for example a $C_8$–$C_{40}$-alkyl radical. This can be saturated or unsaturated, linear or branched. Suitable substituents are, for example, F, Cl, Br or I or a hydroxyl or amino group. This definition also includes substitution of a carbon atom of the alkyl chain by one or more oxygen or nitrogen atoms. $M^{\oplus}$ is a phosphonium or sulfonium ion or a metal cation, such as, for example, an alkali metal ion, such as a sodium or potassium ion. EO is an ethoxy unit and PO is a propoxy unit.

Components which can be used in combination with the sulfonylurea salts in the formulations according to the invention are, for example, known active substances as they are described, for example, in Weed Research 26, 441–445 (1986), or "The Pesticide Manual", 11th edition, The British Crop Protection Council and the Royal Soc. of Chemistry, 1997, and the literature cited therein. Examples of active substances which may be mentioned as herbicides which are known and which can be combined with the sulfonylurea salts are the following (note: either the common names in accordance with the International Organization for Standardization (ISO) or the chemical names, if appropriate together with a customary code number, of the compounds are given):

acetochlor; acifluorfen; acionifen; AKH 7088, i.e. [[[1-[5-[2-chloro-4-(tri-fluoromethyl)phenoxy]-2-nitrophenyl]-2-methoxyethylidene]amino]oxy]-acetic acid and its methyl ester; alachlor; alloxydim; ametryn; amidosulfuron; amitrol; AMS, i.e. ammonium sulfamate; anilofos; asulam; atrazine; azafenidin; azimsulfurone (DPX-A8947); aziprotryn; barban; BAS 516H, i.e. 5-fluoro-2-phenyl-4H-3,1-benzoxazin-4-one; BAS 620H; BAS 65400H; BAY FOE 5043; benazolin; benfluralin; benfuresate; bensulfuron-methyl; bensulide; bentazone; benzofenap; benzofluor; benzoylprop-ethyl; benzthiazuron; bialaphos; bifenox; bispyribac-Na; bromacil; bromobutide; bromofenoxim; bromoxynil; bromuron; buminafos; busoxinone; butachlor; butamifos; butenachlor; buthidazole; butralin; butroxydim; butylate; cafenstrole (CH-900); caloxydim; carbetamide; carfentrazone-ethyl; CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cloransulam-methyl; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters, such as diclofop-methyl; diclosulam, i.e. N-(2,6-dichlorophenyl)-5-ethoxy-7-fluoro-[1,2,4]triazolo[1,5-c]pyrimidine-2-sulfonamide; diethatyl; difenoxuron; difenzoquat; diflufenican; diflufenzopyr (BAS 654 00H), dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL77, i.e. 5-cyano-1-(1,1-dimethylethyl)-N-methyl-1H-pyrazole-4-carboxamide; endothal; EPTC;

esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); flupyrsulfuron-methyl-sodium; fluridone; flurochloridone; fluroxypyr; flurtamone; fluthiacet-methyl; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox; imazapyr; imazaquin and salts, such as the ammonium salt; imazethamethapyr; imazethapyr; imazosulfuron; indanofan (MK-243), ioxynil; isocarbamid; isopropalin; isoproturon; isouron; isoxaben; iodosulfuron, isoxaflutole; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron; oxazidomefone (MY-100); oxyfluorfen; paraquat; pebulate; pendimethalin; pentoxazone (KPP-314); perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyroflufen-ethyl; pyrazolinate; pyrazon; pyrazosu lfu ron-ethyl; pyrazoxyfen; pyribenzoxim (LGC-40836); pyributicarb; pyridate; pyriminobac-methyl; pyrithiobac (KIH-2031); pyroxofop and its esters (for example propargyl ester); quinclorac; quinmerac; quinofop and its ester derivatives, quizalofop and quizalofop-P and their ester derivates, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; sec-bumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron-methyl; sulfosate (IC1-A0224); sulfosulfuron; TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimine (SN-24085); thifensulfuron-methyl; thiobencarb; tiocarbazil; tralkoxydim; tri-allate; triasulfuron; triaziflam; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; JTC-101; UBH-509; D-489; LS82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are in commercially available form, are, if appropriate, diluted in the customary manner, for example using water in the case of wettable powders, emulsifiable concentrates, dispersions and water-dispersible granules.

In general, the formulations according to the invention comprise 0.1 to 99% by weight, in particular 0.1 to 95% by weight, of active substance, preferably a sulfonylurea salt of the formula (Ia). The active substance concentration in wettable powders is, for example, approximately 10 to 90% by weight, the remainder to 100% by weight being composed of customary formulation components. In the case of emulsifiable concentrates, the active substance concentration may amount to approximately 1 to 90, preferably 5 to 80, % by weight. Formulations in the form of dusts comprise 1 to 30% by weight of active substance, in most cases preferably 5 to 20% by weight of active substance, and sprayable solutions comprise approximately 0.05 to 80, preferably 2 to 50, % by weight of active substance. The active substance content of water-dispersible granules depends partly on whether the active compound is in liquid or solid form and on which granulation auxiliaries, fillers and the like are being used. The active substance content of the water-dispersible granules amounts to, for example, between 1 and 95% by weight, preferably between 10 and 80% by weight.

Formulations in the form of dusts, granules for soil application or for broadcasting and sprayable solutions are conventionally not diluted any more with inert substances prior to use.

The proportion of sulfonylurea salts in the EC formulations according to the invention is generally 0.01–70% by weight, preferably 0.1–70% by weight, particularly preferably 0.1–50% by weight. In addition, the formulations can comprise further agrochemicals from the field of crop protection—for example herbicides, fungicides, insecticides, growth regulators, safeners or fertilizers—in an amount of from 0 to 70% by weight. They can also comprise from 1 to 40% by weight, preferably 2–40% by weight, of a surfactant system. The surfactant system can be composed, for example, of a) one or more nonionic surfactants, b) one or more betainic surfactants, c) one or more anionic surfactants, d) one or more cationic surfactants, or e) a mixture of the surfactants mentioned under a)–d).

The EC formulations can comprise from 0 to 95% by weight, preferably from 5 to 95% by weight, of a solvent system. Suitable solvent systems are, for example, a) a nonpolar solvent, for example aromatic hydrocarbons such as Solvesso®, esters of long-chain saturated or unsaturated (fatty) acids and/or alcohols, such as, for example, rapeseed oil methyl ester, or a mixture of nonpolar solvents b) a polar protic or aprotic solvent, for example gamma-butyrolactone, propylene carbonate, propionitrile or methanol, ethanol, or else mixtures thereof or c) mixtures of the solvent systems mentioned above under a) and b).

In addition, the EC formulations according to the invention may optionally comprise 3–90% by weight of a wetting agent, which may have bioactivating properties, or else a mixture of different wetting agents, which may have bioactivating properties.

The formulations may optionally comprise further stabilizing compounds, for example pH-stabilizing reagents (for example pH 5–9), substances having antifoam properties, acid scavengers, water scavengers or crystallization inhibitors.

A further embodiment of the formulations according to the invention is characterized by the fact that it is a dispersion, where the liquid homogeneous phase is composed as described above and in which one or more insoluble compounds are dispersed. The insoluble compounds can be agrochemicals, such as, for example, herbicides, insecticides, fungicides, safeners or fertilizers, or else formulation auxiliaries, such as, for example, surfactants which are insoluble in the organic phase, such as, for example, Netzer IS (from Clariant).

The EC formulations according to the invention are preferably characterized by the fact that the proportion of sulfonfylurea salt, in particular of the formula (Ia), or of the mixture of sulfonylurea salts is generally 0.1–70.0% by weight, preferably 0.1–50.0% by weight. Suitable solvents are polar solvents, such as, for example, gamma-butyrolactone, acetonitrile, propionitrile; their proportion is 5.0–95.0% by weight. To obtain a stable emulsion after addition to water, the finished EC product should comprise a proportion by weight of 2.0–40.0% by weight of a mixture of one anionic and one nonionic surfactant or a mixture of cationic and nonionic surfactants. In addition, it is possible to add, if appropriate, other components to the EC formulations: by adding 1.0–90.0% by weight of a hydrophobic solvent, it is possible to modify the emulsion formation in aqueous spray mixtures advantageously. Suitable solvent components are, for example, rapeseed oil methyl ester, aromatic solvents such as, for example, Solvesso, esters of long-chain acids and alcohols, or else mixtures of hydrophobic solvents.

The EC formulations thus described may optionally comprise 3.0–90.0% by weight of a wetting agent, which may have bioactivating properties, or of a mixture of wetting agents.

Agrochemical combination preparations can be obtained by adding 20.0–50.0% by weight of agrochemically active compounds which are chemically inert to sulfonylurea salts and readily soluble in the solvent systems which are typical for the formulation type according to the invention. This is the case for a large number of commercial agrochemicals. The formulations according to the invention may optionally also comprise stabilizers which, for example, stabilize the pH of the tank mix at between 6 and 8.

EC formulations according to the invention preferably have the following composition:

1) the sulfonylurea salt content is generally 0.1–70.0% by weight, preferably 0.1–50.0% by weight; the formulation may comprise one or more active compounds 2) the formulation may optionally comprise between 0 and 50.0% by weight of other agrochemicals (herbicides, insecticides, fungicides, growth regulators, safeners, fertilizers), 3) 5.0–95.0% by weight of a polar solvent, such as, for example, gamma-butyrolactone, acetonitrile, propionitrile, propylene carbonate, or else mixtures thereof 4) optionally 1.0–90.0% by weight of a hydrophobic solvent, for example rapeseed oil methyl ester, aromatic solvents, esters of long-chain acids and alcohols 5) 2.0–40.0% by weight of a mixture of anionic and nonionic compounds or 6) 2.0–40.0% by weight of a mixture of cationic and nonionic compounds 7) optionally 3.0–90.0% by weight of a wetting agent, which may have bioactivating properties, or of a mixture of different wetting agents, which may have bioactivating properties, 8) optionally other stabilizing agents—for example pH-stabilizing reagents (pH between 6 and 8), substances having antifoam properties, substances which can serve as acid scavengers, water scavengers or crystallization inhibitors.

To prepare an EC formulation, it is possible to dissolve, for example, from 0.1 to 15.0% by weight of a sulfonylurea salt in from 15.0 to 25.0% by weight of propylene carbonate and from 30.0 to 50.0% by weight of an aromatic compound or a mixture of aromatic compounds (boiling range 219–282° C.) with stirring at 20° C.–30° C.

After the sulfonylurea salt has been completely dissolved, from 5.0 to 15.0% by weight of the calcium or sodium salt of dodecylbenzenesulfonic acid or of a salt mixture, from 5.0 to 15.0% by weight of a ($C_{12}$–$C_{18}$)-fatty acid polyglycol ester 40 EO and from 15.0 to 20.0% by weight of a fatty alcohol polyglycol ether are added with stirring to the solution.

If appropriate, a water scavenger, an acid scavenger, and antifoam or a crystallization inhibitor may also be added.

The sulfonylurea salts comprised in the formulations according to the invention, for example those of the formula (Ia) can be prepared from known sulfonylureas or sulfonylurea metal salts, in particular alkali metal salts (see, for example, EP-A-30138, EP-A-7687), or else from sulfonamide salts, for example by the following routes:

1) Deprotonation of neutral sulfonylureas, for example of the formula (XIII), with a suitable base of the formula $M^+B^-$ (Eq. 1), where $B^{31}$ is, for example, hydroxyl or alkoxy anions, such as methoxy, ethoxy, $^n$propoxy, $^i$propoxy, $^n$butoxy or $^t$butoxy, or anions of formulation auxiliaries which carry at least one OH group, for example alkoxides, which can be alkoxylated, for example ethoxylated or propoxylated, such as $C_8H_{17}(OCH_2CH_2)O^\ominus$, and where $M^+$ is a phosphonium or sulfonium ion.

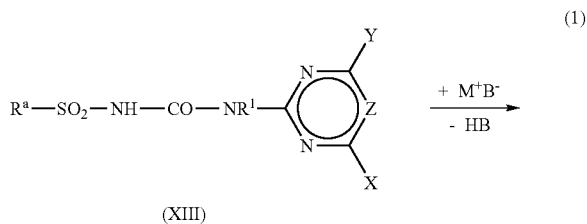

(XIII)

-continued

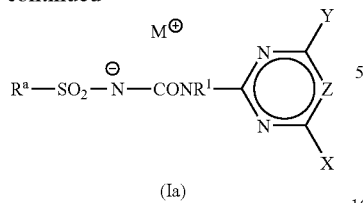

(Ia)

To this end, the sulfonylurea, for example of the formula (XIII), is dissolved or suspended in an inert solvent or solvent mixture and reacted with one equivalent of $M^+B^-$ at temperatures between $-20°$ C. and $100°$ C., preferably between $-10°$ C. and $50°$ C.

2) Cation exchange of metal salts of sulfonylureas, for example of the formula (XIV), in which $Met^{\oplus}$ is a metal cation, preferably an alkali metal ion, such as $Na^+$ or $K^+$, with suitable reagents of the formula $M^+X'^-$ (Eq. 2), where $M^{+'}$ is a phosphonium or sulfonium ion and $X'^-$ is an anion, for example a halide anion, such as $F^-$, $Cl^-$ or $Br^{31}$, or a phosphate, sulfate or carboxylate anion, where this definition includes inorganic and organic salts, as are customarily used, for example, in surfactant chemistry (for example organic phosphate anions, phosphonate anions, sulfate anions, sulfonate anions, carboxylates).

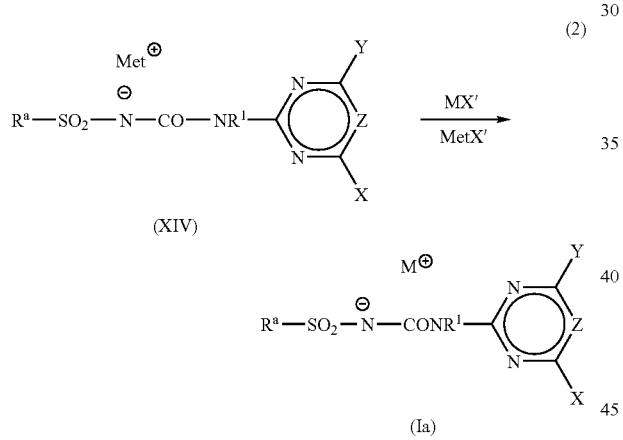

To this end, the metal salts, for example alkali metal salts (for example $Met^{\oplus}=Na^+$, $K^+$), which are known from the literature or prepared in a manner known from the literature, of the corresponding sulfonylureas are dissolved in an inert solvent or solvent mixture and reacted with one equivalent of the reagent $M^+X'^-$. After the reaction has ended, the salt, for example the alkali metal salt (such as NaCl), which is obtained as a by-product, can be removed by filtration.

3) In situ deprotonation and cation exchange (Eq. 3), starting from neutral sulfonylureas, for example of the formula (XIII), with suitable reagents a) of the formula $M^+X'^-$, where $M^+$ is a phosphonium or sulfonium ion and $X'^{31}$ is an anion, for example a halide anion, such as $F^-$, $Cl^-$ or $Br^-$, or a phosphate, sulfate or carboxylate anion, where this definition includes inorganic and organic salts, as are customarily used, for example, in surfactant chemistry (for example organic phosphate anions, phosphonate anions, sulfate anions, sulfonate anions, carboxylates) and b) of the formula MetB, where Met is a metal cation, in particular an alkali metal cation, such as $Na^+$ or $K^+$, and B is a suitable base, for example a hydroxy or alkoxy anion, such as methoxy, ethoxy, $^n$propoxy, $^i$propoxy or $_n$butoxy.

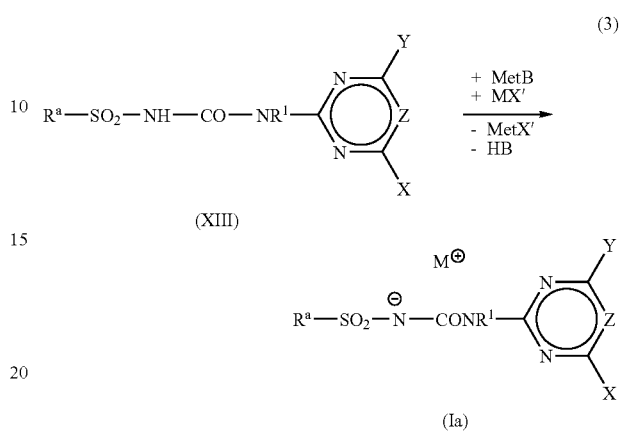

To this end, the sulfonylurea is dissolved in an inert solvent or solvent mixture and reacted with one equivalent each of the reagents $M^+X'^-$ and MetB. After the reaction has ended, the metal salt, in particular alkali metal salt (for example NaCl) which is obtained as a by-product, can be removed by filtration.

4) Reaction of a sulfonamide salt, for example of the formula XV, with an isocyanate, for example of the formula XVI (Eq. 4).

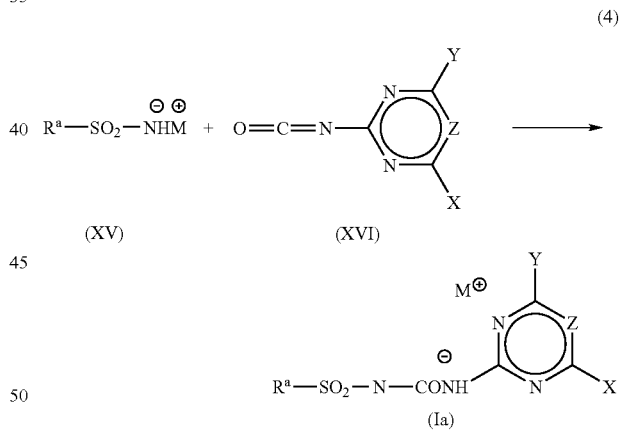

The reaction is carried out in an inert solvent or solvent mixture—such as, for example, tetrahydrofuran (THF)— at temperatures between $-20°$ C. and $100°$ C., preferably between $-10°$ C. and $70°$ C., by reacting equimolar amounts of the isocyanate, for example of the formula XVI, with the sulfonamide salt, for example of the formula XV. The sulfonamide salt, for example of the formula XV, can be employed directly or formed in situ—for example by reacting the corresponding sulfonamide with a suitable base $M^+X'^-$, where $M^+$ is a phosphonium or sulfonium ion and $X^-$ is, for example, a hydroxy or alkoxy anion. Isocyanates, for example of the formula XVI, are well known from the literature. These reactions always lead to compounds in which $R^1$ is hydrogen.

5) Reaction of a sulfonamide salt, for example of the formula XV, with a carbamate, for example of the formula XVII (Eq. 5).

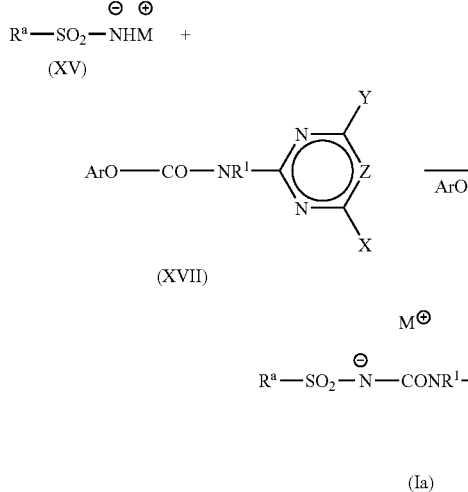

The reaction is carried out in an inert solvent (or solvent mixture)—such as tetrahydrofuran—at temperatures between −20° C. and 100° C., preferably between −10° C. and 70° C., by reacting equimolar amounts of the carbamate, for example of the formula XVII, with the sulfonamide salt, for example of the formula XV. The sulfonamide salt, for example of the formula XV, can be employed directly or formed in situ—for example by reacting the corresponding sulfonamide with a suitable base $M^+X^-$, where $M^+$ is a phosphonium or sulfonium ion and $X^-$ is, for example, a hydroxy or alkoxy anion. Carbamates, for example of the formula XVII, are well known from the literature. In the formula XVII, Ar is a substituted or unsubstituted aromatic radical, such as phenyl or 2,4-dichlorophenyl.

This reaction is carried out at temperatures of from −20° C. to +100° C., preferably between −10° C. and 50° C., in inert solvents, such as, for example, THF, $CH_2Cl_2$ or MeOH or solvent mixtures.

The definitions used in the Preparation Processes 1) to 5) have—unless indicated otherwise—the same meaning as given above for the formulae Ia and Ib.

Inert solvents means that the solvents or solvent mixtures used are chemically inert under the reaction conditions mentioned.

Using the Preparation Processes 1) to 5), it is possible to prepare and isolate the sulfonylurea salts in a simple manner. Alternatively, the sulfonylurea salts can also be prepared by Processes 1), 2) and 3) even during the formulation process.

The preparation processes of the compounds of the formula (Ia) according to the invention are likewise novel and also form part of the subject matter of this invention.

The preparation processes mentioned above can be used to prepare, for example, the compounds listed in the tables below.

Compounds of the formula (A) below are listed in Table 1:

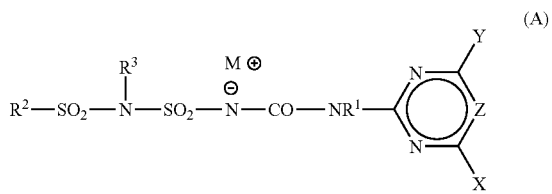

TABLE 1

| Ex. | $R^1$ | $R^2$ | $R^3$ | $M^\oplus$ | X | Y | Z |
|---|---|---|---|---|---|---|---|
| 1 | H | Me | Me | $S^\oplus Me_3$ | OMe | OMe | CH |
| 2 | H | Me | Me | $S^\oplus Ph_3$ | OMe | OMe | CH |
| 3 | H | Me | Me | $P^\oplus Ph_4$ | OMe | OMe | CH |
| 4 | H | Me | Me | $PPh_3CH_2Ph^\oplus$ | OMe | OMe | CH |
| 5 | H | Me | Me | $PPh_3Me^\oplus$ | OMe | OMe | CH |

Compounds of the formula (B) below are listed in Table 2:

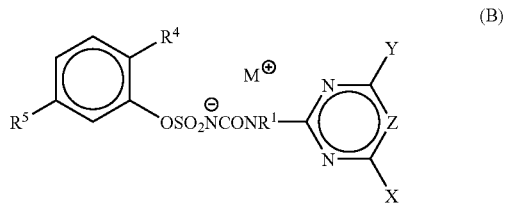

TABLE 2

| Ex. | $R^1$ | $R^4$ | $R^5$ | $M^\oplus$ | X | Y | Z |
|---|---|---|---|---|---|---|---|
| 1 | H | OEt | H | $SMe_3^\oplus$ | OMe | OMe | CH |
| 2 | H | OEt | H | $SPh_3^\oplus$ | OMe | OMe | CH |
| 3 | H | OEt | H | $PPh_4^\oplus$ | OMe | OMe | CH |
| 4 | H | OEt | H | $PPh_3Me^\oplus$ | OMe | OMe | CH |

Compounds of the formula (C) below are listed in Table 3:

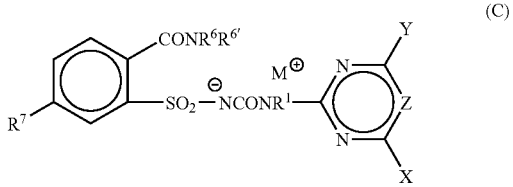

TABLE 3

| Ex. | $R^1$ | $NR^6R^{6'}$ | $R^7$ | $M^\oplus$ | X | Y | Z |
|---|---|---|---|---|---|---|---|
| 1 | H | $NMe_2$ | NHCOOMe | $SMe_3^\oplus$ | OMe | OMe | CH |
| 2 | H | $NMe_2$ | NHCOOMe | $SPh_3^\oplus$ | OMe | OMe | CH |
| 3 | H | $NMe_2$ | NHCOOMe | $PPh_4^\oplus$ | OMe | OMe | CH |
| 4 | H | $NMe_2$ | NHCOOMe | $PPh_3Me^\oplus$ | OMe | OMe | CH |
| 5 | H | $NMe_2$ | NHCHO | $SMe_3^\oplus$ | OMe | OMe | CH |

TABLE 3-continued

| Ex. | R¹ | NR⁶R⁶' | R⁷ | M⊕ | X | Y | Z |
|---|---|---|---|---|---|---|---|
| 6 | H | NMe₂ | NHCHO | SPh₃⊕ | OMe | OMe | CH |
| 7 | H | NMe₂ | NHCHO | PPh₄⊕ | OMe | OMe | CH |
| 8 | H | NMe₂ | NHCHO | PPh₃Me⊕ | OMe | OMe | CH |
| 9 | H | NMe₂ | NHCOCH₃ | SMe₃⊕ | OMe | OMe | CH |
| 10 | H | NMe₂ | NHCOCH₃ | SPh₃⊕ | OMe | OMe | CH |
| 11 | H | NMe₂ | NHCOCH₃ | PPh₄⊕ | OMe | OMe | CH |
| 12 | H | NMe₂ | NHCOCH₃ | PPh₃Me⊕ | OMe | OMe | CH |

Compounds of the formula (D) below are listed in Table 4:

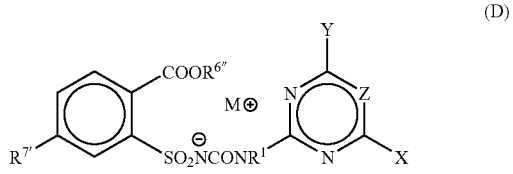

(D)

TABLE 4

| Ex. | R¹ | R⁶" | R⁷' | M⊕ | X | Y | Z |
|---|---|---|---|---|---|---|---|
| 1 | H | Me | I | SMe₃⊕ | Me | OMe | N |
| 2 | H | Me | I | SPh₃⊕ | Me | OMe | N |
| 3 | H | Me | I | PPh₄⊕ | Me | OMe | N |
| 4 | H | Me | I | PPh₃Me⊕ | Me | OMe | N |
| 5 | H | Me | CH₂NHCHO | SMe₃⊕ | OMe | OMe | CH |
| 6 | H | Me | CH₂NHCHO | SPh₃⊕ | OMe | OMe | CH |
| 7 | H | Me | CH₂NHCHO | PPh₄⊕ | OMe | OMe | CH |
| 8 | H | Me | CH₂NHCHO | PPh₃Me⊕ | OMe | OMe | CH |
| 9 | H | Me | CH₂NH—COOMe | SMe₃⊕ | OMe | OMe | CH |
| 10 | H | Me | CH₂NH—COOMe | SPh₃⊕ | OMe | OMe | CH |
| 11 | H | Me | CH₂NH—COOMe | PPh₄⊕ | OMe | OMe | CH |
| 12 | H | Me | CH₂NH—COOMe | PPh₃Me⊕ | OMe | OMe | CH |
| 13 | H | Me | CH₂NH—SO₂Me | SMe₃⊕ | OMe | OMe | CH |
| 14 | H | Me | CH₂NH—SO₂Me | SPh₃⊕ | OMe | OMe | CH |
| 15 | H | Me | CH₂NH—SO₂Me | PPh₄⊕ | OMe | OMe | CH |
| 16 | H | Me | CH₂NH—SO₂Me | PPh₃Me⊕ | OMe | OMe | CH |
| 17 | H | Me | CH₂NMeSO₂Me | SMe₃⊕ | OMe | OMe | CH |
| 18 | H | Me | CH₂NMeSO₂Me | SPh₃⊕ | OMe | OMe | CH |
| 19 | H | Me | CH₂NMeSO₂Me | PPh₄⊕ | OMe | OMe | CH |
| 20 | H | Me | CH₂NMeSO₂Me | PPh₃Me⊕ | OMe | OMe | CH |
| 21 | H | Me | I | SMe₃⊕ | OMe | OMe | N |
| 22 | H | Me | I | SPh₃⊕ | OMe | OMe | N |
| 23 | H | Me | I | PPh₄⊕ | OMe | OMe | N |
| 24 | H | Me | I | PPh₃Me⊕ | OMe | OMe | N |
| 25 | Me | Me | H | SMe₃⊕ | OMe | Me | N |
| 26 | Me | Me | H | SPh₃⊕ | OMe | Me | N |
| 27 | Me | Me | H | PPh₄⊕ | OMe | Me | N |
| 28 | Me | Me | H | PPh₃Me⊕ | OMe | Me | N |
| 29 | H | Me | H | SMe₃⊕ | OMe | Me | N |
| 30 | H | Me | H | SPh₃⊕ | OMe | Me | N |
| 31 | H | Me | H | PPh₄⊕ | OMe | Me | N |

TABLE 4-continued

| Ex. | R¹ | R⁶" | R⁷' | M⊕ | X | Y | Z |
|---|---|---|---|---|---|---|---|
| 32 | H | Me | H | PPh₃Me⊕ | OMe | Me | N |
| 33 | H | Me | F | SMe₃⊕ | OMe | Me | N |
| 34 | H | Me | F | SPh₃⊕ | OMe | Me | N |
| 35 | H | Me | F | PPh₄⊕ | OMe | Me | N |
| 36 | H | Me | F | PPh₃Me⊕ | OMe | Me | N |
| 37 | H | Me | Cl | SMe₃⊕ | OMe | Me | N |
| 38 | H | Me | Cl | SPh₃⊕ | OMe | Me | N |
| 39 | H | Me | Cl | PPh₄⊕ | OMe | Me | N |
| 40 | H | Me | Cl | Ph₃Me⊕ | OMe | Me | N |

Compounds of the Formula (E) below are listed in Table 5:

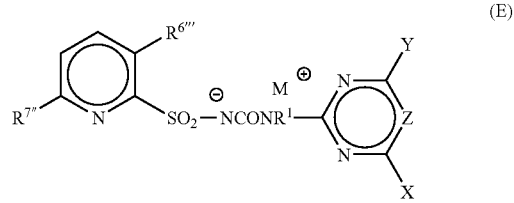

(E)

TABLE 5

| Ex. | R¹ | R⁶''' | R⁷'' | M⊕ | X | Y | Z |
|---|---|---|---|---|---|---|---|
| 1 | H | Me | Cl | PPh₃Me⊕ | OMe | Me | N |
| 2 | H | NMeSO₂Me | H | SMe₃⊕ | OMe | OMe | CH |
| 3 | H | NMeSO₂Me | H | SPh₃⊕ | OMe | OMe | CH |
| 4 | H | NMeSO₂Me | H | PPh₄⊕ | OMe | OMe | CH |
| 5 | H | NMeSO₂Me | H | PPh₃Me⊕ | OMe | OMe | CH |
| 6 | H | NHSO₂Me | H | SMe₃⊕ | OMe | OMe | CH |
| 7 | H | NHSO₂Me | H | SPh₃⊕ | OMe | OMe | CH |
| 8 | H | NHSO₂Me | H | PPh₄⊕ | OMe | OMe | CH |
| 9 | H | NHSO₂Me | H | PPh₃Me⊕ | OMe | OMe | CH |
| 10 | H | NEtCOCH₃ | H | SMe₃⊕ | OMe | OMe | CH |
| 11 | H | NEtCOCH₃ | H | SPh₃⊕ | OMe | OMe | CH |
| 12 | H | NEtCOCH₃ | H | PPh₄⊕ | OMe | OMe | CH |
| 13 | H | NEtCOCH₃ | H | PPh₃Me⊕ | OMe | OMe | CH |
| 14 | H | NEtCHO | H | SMe₃⊕ | OMe | OMe | CH |
| 15 | H | NEtCHO | H | SPh₃⊕ | OMe | OMe | CH |
| 16 | H | NEtCHO | H | PPh₄⊕ | OMe | OMe | CH |
| 17 | H | NEtCHO | H | PPh₃Me⊕ | OMe | OMe | CH |
| 18 | H | NⁿPrCHO | H | SMe₃⊕ | OMe | OMe | CH |
| 19 | H | NⁿPrCHO | H | SPh₃⊕ | OMe | OMe | CH |
| 20 | H | NⁿPrCHO | H | PPh₄⊕ | OMe | OMe | CH |
| 21 | H | NⁿPrCHO | H | PPh₃Me⊕ | OMe | OMe | CH |

The compounds of the formula (Ia) according to the invention and the formulations according to the invention can be employed as herbicides against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being restricted to certain species. Examples of weed species on which the active compounds and formulations act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Matricaria, Abutilon* and *Sida* from amongst the annuals, and *Convolvulus, Cirsium, Rumex* and *Artemisia* in the case of the perennial weeds.

The active compounds according to the invention also effect outstanding control of harmful plants which occur under the specific conditions of rice growing such as, for example, *Echinochloa, Sagittaria, Alisma, Eleocharis, Scirpus* and *Cyperus*.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds and formulations according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. For these reasons, the present compounds are highly suitable for selectively controlling undesired plant growth in plantings for agricultural use or in plantings of ornamentals.

The substances and formulations according to the invention furthermore have outstanding growth-regulating properties on crop plants. They intervene in a regulatory manner in the endogenous metabolism of the plant and can thus be employed for influencing plant contents in a controlled manner and for facilitating harvesting, such as, for example, by triggering desiccation and stunting growth. They are furthermore also suitable for general control and inhibition of undesirable vegetative growth without killing the plants at the same time. Inhibition of vegetative growth plays a major role in many mono- and dicotyledonous crops, since lodging can be reduced or completely prevented by this means.

Owing to their herbicidal and plant growth-regulatory properties, the active compounds and formulations can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storability, composition and to specific ingredients of the harvested product. Thus, transgenic plants having an increased starch content or a modified quality of the starch or those having a different fatty acid composition of the harvested product are known.

The use of the compounds and formulations according to the invention in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred.

The formulations and compounds according to the invention can preferably be used as herbicides in crops of useful plants which are resistant or which have been made resistant by genetic engineering toward the phytotoxic effects of the herbicides.

Conventional ways of preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of

- genetically engineered changes in crop plants in order to modify the starch synthesized in the plants (for example WO 92/11376, WO 92/14827, WO 91/19806),
- transgenic crop plants which are resistant to certain herbicides of the glufosinate-type (cf., for example, EP-A 0 242 236, EP-A 0 242 246) or glyphosate-type (WO 92/00377), or of the sulfonylurea-type (EP-A 0 257 993, U.S. Pat. No. 5,013,659),
- transgenic crop plants, for example cotton, having the ability to produce *Bacillus thuringiensis* toxins (Bt toxins) which impart to the plants resistance to certain pests (EP-A 0 142 924, EP-A 0 193 259),
- transgenic crop plants having a modified fatty acid composition (WO 91/13972).

Numerous molecular-biological techniques which allow the preparation of novel transgenic plants having modified properties are known in principle; see, for example, Sambrook et al., 1989, Molecular Cloning, A Laboratory Manual, 2nd ed., Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431).

In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end, it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to whole plants using known techniques. The transgenic plants can in principle be plants of any desired plant species, i.e. both monocotyledonous and dicotyledonous plants.

In this manner, it is possible to obtain transgenic plants which have modified properties by overexpression, suppression or inhibition of homologous (=natural) genes or gene sequences or by expression of heterologous (=foreign) genes or gene sequences.

The compounds and formulations according to the invention can preferably be used in transgenic crops which are resistant to herbicides from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crop is resistant, and an effect on the growth and the yield of the transgenic crop plants.

The invention therefore also provides for the use of the formulations according to the invention and the compounds of the formula (Ia) according to the invention as herbicides or plant growth regulators.

The EC formulations according to the invention have the advantage that they are generally very user-friendly and can be prepared at low costs. Moreover, this formulation type in principle offers the possibility to prepare combination preparations in a simple and cost-effective manner, provided that the combination partner is soluble in the desired concentration in the chosen organic solvent system and is chemically inert.

The formulations according to the invention, in particular the EC formulations, have high chemical stability. Moreover, the formulations according to the invention, in particular the EC formulations, can, in addition to the chemical stability, also have "higher loading" (a higher concentration) of the formulation of active compound salts. The formulations according to the invention can furthermore be prepared both as a liquid formulation (for example EC formulation) or as a solid formulation (for example WP or WG formulation).

EXAMPLES

Formulation Examples

The formulations mentioned in Table I are obtained by initially charging the solvent Dowanol PM at room temperature and admixing successively with mechanical stirring the sulfonylurea component and the auxiliaries mentioned.

The examples of Table I show that, using specific sulfonylurea salts, it is possible to prepare stable EC formulations having an economically attractive loading of active compound(s), in contrast to the corresponding neutral sulfonylureas or their metal salts.

TABLE I

|  | Formulation 1 | Formulation 2 | Formulation 3 | Formulation 4 | Formulation 5 | Formulation 6 | Formulation 7 |
| --- | --- | --- | --- | --- | --- | --- | --- |
| Iodosulfuron* | 10.0% | — | — | — | — | — | — |
| Comp. 4.2 | — | 11.4% | — | — | — | — | — |
| Foramsulfuron** | — | — | 5.0% | — | — | — | — |
| Comp. 3.6 | — | — | — | 6.2% | 6.2% | — | — |
| Neutral compound of Comp. 4.14 | — | — | — | — | — | 5.0% | — |
| Comp. 4.14 | — | — | — | — | — | — | 5.9% |
| 1-Methoxy-2-propanol (Dowanol PM) | 80.0% | 78.6% | 85.0% | 83.8% | 83.8% | 85.0% | 84.1% |
| Genapol X-060 methyl ether | 10.0% | 10.0% | 10.0% | 10.0% | — | 10.0% | 10.0% |
| Rapeseed oil methyl ester (Edenor MESU) | — | — | — | — | 10.0% | — | — |
| Total | 100.0% no EC | 100.0% EC | 100.0% no EC | 100.0% EC | 100.0% EC | 100.0% no EC | 100.0% EC |

*Neutral compound of Comp. 4.2,
**Neutral compound of Comp. 3.6.

The invention claimed is:

1. A formulation comprising:

a) at least one sulfonylurea salt of the formula (Ia):

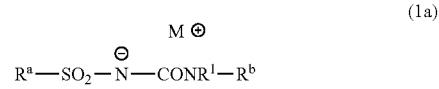

wherein $R^1$ is H or $C_1$–$C_{10}$-hydrocarbon radical, $R^a$ is a radical of the formula (IVa) or (IVb):

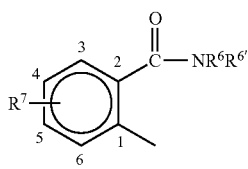

IVa

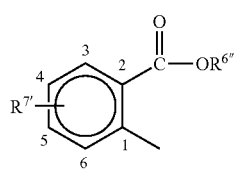

IVb $R^6$ and $R^{6'}$ are identical or different and are H or a substituted or unsubstituted $C_1$–$C_{20}$-hydrocarbon radical, where $R^6$ and $R^{6'}$ may form an unsubstituted or substituted ring, $R^7$ is H, halogen, OH, $NR^xR^y$, in which $R^x$ and $R^y$ are H or $(C_1$–$C_3)$-alkyl, or $R^7$ is N—$(C_1$–$C_3)$-alkyl-N-acylamino or N-acylamino or a substituted or unsubstituted $C_1$–$C_{20}$-hydrocarbon radical or hydrocarbonoxy radical, $R^{6'}$ is a substituted or unsubstituted $C_1$–$C_{20}$-hydrocarbon radical, $R^{7'}$ is H, halogen, OH, $NR^xR^y$, in which $R^x$ and $R^y$ are H or $(C_1$–$C_3)$-alkyl, or $R^{7'}$ is N—$(C_1$–$C_3)$-alkyl-N-acylamino, N-acylamino or a substituted or unsubstituted $C_1$–$C_{20}$-hydrocarbon radical or a $C_1$–$C_{20}$-hydrocarbonoxy radical, is a radical of the formula:

$M^+$ is $SMe_3$ $R^b$ is a radical of the formula:

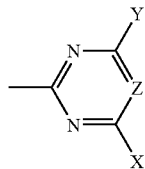

wherein

X is substituted or unsubstituted $(C_1$–$C_6)$-alkyl, substituted or unsubstituted $(C_1$–$C_6)$-alkoxy, halogen, substituted or unsubstituted $(C_1$–$C_6)$-mercaptoalkyl or $(C_1$–$C_3)$-mono- or $(C_1$–$C_3)$-dialkylamino, Y is substituted or unsubstituted $(C_1$–$C_6)$-alkyl, substituted or unsubstituted $(C_1$–$C_6)$-alkoxy, halogen, substituted or unsubstituted $(C_1$–$C_6)$-mercaptoalkyl or $(C_1$–$C_3)$-mono- or $(C_1$–$C_3)$-dialkylamino, and Z is N b) customary auxiliaries and additives.

2. The formulation according to claim 1, wherein $R^1$ is a substituted or unsubstituted $(C_1$–$C_6)$-alkyl.

3. The formulation according to claim 1, wherein the formulation is an emulsifiable concentrate.

4. The formulation according to claim 1, wherein $R^4$ is a $(C_1$–$C_6)$-alkyl, $(C_2$–$C_6)$-alkenyl, $(C_2$–$C_6)$-alkynyl, $(C_1$–$C_6)$-alkoxy, $(C_3$–$C_6)$-alkenyloxy or a $(C_3$–$C_6)$-alkynyloxy, substituted or unsubstituted by one or more radicals.

5. The formulation according to claim 4, wherein said radical is halogen or $(C_1$–$C_3)$-alkoxy.

6. The formulation according to claim 1, wherein $R^5$ is a $(C_1$–$C_6)$-alkyl.

7. The formulation according to claim 1, wherein $R^6$ and $R^{6'}$ are $C_1$–$C_6$-alkyl.

8. The formulation according to claim 7, wherein said $C_1$–$C_6$-alkyl is Me, Et, $^nPr$, $^iPr$ or $^cPr$.

9. The formulation according to claim 1, wherein $R^7$ is a $(C_1$–$C_3)$-alkyl, $(C_1$–$C_3)$-haloalkyl, halogen, $(C_1$–$C_3)$-alkyl-(N—$(C_1$–$C_3)$-alkyl-N-acylamino), $(C_1$–$C_3)$-alkyl-(N-acylamino) or $(C_1$–$C_3)$-alkoxy.

10. The formulation according to claim 1, wherein $R^{6''}$ is a substituted or unsubstituted $(C_1$–$C_6)$-alkyl, substituted or unsubstituted $(C_3$–$C_6)$-alkenyl, substituted or unsubstituted $(C_3$–$C_6)$-cycloalkyl, substituted or unsubstituted $(C_3$–$C_7)$-alkynyl, or a substituted or unsubstituted $(C_4$–$C_8)$-cycloalkylalkyl.

11. The formulation according to claim 1, wherein $R^{7'}$ is a $(C_1$–$C_3)$-alkyl, $(C_1$–$C_3)$-haloalkyl, $(C_1$–$C_3)$-alkyl-(N—$(C_1$–$C_3)$-alkyl-N-acylamino), $(C_1$–$C_3)$-alkyl-(N-acylamino) or $(C_1$–$C_3)$-alkoxy.

12. A compound of the formula (Ia) as defined in claim 1 wherein:

$R^1$ is H or Me, $R^6$ and $R^{6'}$ are identical or different $C_1$–$C_6$-alkyl radicals, $R^7$ is H, Me, Et, $CF_3$, F, CL, Br, I, $N[(C_1$–$C_3)$-alkyl]-$R^8$, NH—$R^9$, $CH_2N[(C_1$–$C_3)$-alkyl]-$R^{10}$, $CH^2NH$—$R^{11}$, $CH_2CH_2N[(C_1$–$C_3)$-alkyl]-$R^{12}$, $CH_2CH_2NH$—$R^{13}$, wherein the radicals $R^8$ to $R^{13}$ are H, $(C_1$–$C_6)$-alkyl, $(C_1$–$C_6)$-haloalkyl, CHO, $COO(C_1$–$C_6)$-alkyl, COO$(C_1$–$C_6)$-haloalkyl, $SO_2$—$(C_1$–$C_6)$-alkyl, $SO_2$—$(C_1$–$C_6)$-haloalkyl, CO—$(C_1$–$C_6)$-alkyl or CO—$(C_1$–$C_6)$-haloalkyl, $R^{6''}$ is Me, Et, $^nPr$, $^iPr$, $^cPr$, $^nBu$, $^iBu$, $^sBu$, $^tBu$, $^cBu$, $R^{7'}$ is H, Me, Et, $CF_3$, F, CL, Br, I, $N[(C_1$–$C_3)$-alkyl]-$R^8$, NH—$(C_1$–$C_3)$-alkyl, $CH_2N[(C_1$–$C_3)$-alkyl]-$R^{10}$, $CH_2NH$—$R^{11}$, $CH_2CH_2N[(C_1$–$C_3)$-alkyl]-$R^{12}$, $CH_2CH_2NH$—$R^{13}$, wherein the radicals $R^8$ and $R^{10}$ to $R^{13}$ are H, $(C_1$–$C_6)$-alkyl, $(C_1$–$C_6)$-haloalkyl, CHO, $COO(C_1$–$C_6)$-alkyl, $COO(C_1$–$C_6)$-haloalkyl, $SO_2$—$(C_1$–$C_6)$-alkyl, $SO_2$—$(C_1$–$C_6)$-haloalkyl, CO—$(C_1$–$C_6)$-alkyl or CO—$(C_1$–$C_6)$-haloalkyl, $M^+$ is $SMe_3$ $R^b$ is a radical of the formula:

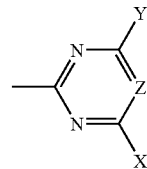

wherein

X is substituted or unsubstituted $(C_1$–$C_6)$-alkyl, substituted or unsubstituted $(C_1$–$C_6)$-alkoxy, halogen, substituted or unsubstituted $(C_1$–$C_6)$-mercaptoalkyl or $(C_1$–$C_3)$-mono- or $(C_1$–$C_3)$-dialkylamino, Y is substituted or unsubstituted $(C_1$–$C_6)$-alkyl, substituted or unsubstituted $(C_1$–$C_6)$-alkoxy, halogen, substituted or unsubstituted $(C_1$–$C_6)$-mercaptoalkyl or $(C_1$–$C_3)$-mono- or $(C_1$–$C_3)$-dialkylamino, and Z is N.

13. The compound according to claim 12, wherein $R^4$ is Me, Et, OMe, OEt or $CF_3$.

14. The compound according to claim 12, wherein said halogen is as F, Cl, Br or I.

15. The compound according to claim 12, wherein $R^6$=Me, $R^{6'}$=Me;

$R^6$=Me, $R^{6'}$=Et and $R^{6'}$=Et, $R^6$=Et.

16. The compound according to claim 12, wherein the radicals $R^7$ in the formula (IVa) which are different from hydrogen are located in the 5-position on the phenyl ring.

17. The compound according to claim 12, wherein $R^{6''}$ is Me or Et.

18. The compound according to claim 12, wherein the radicals $R^{7'}$ in the formula (IVb) which are different from hydrogen are located in the 5-position on the phenyl ring.

19. The compound according to claim 12, wherein X is OMe, OEt, Me or Cl.

20. The compound according to claim 12, wherein Y is OMe, OEt, Me or Cl.

21. An emulsifiable concentrate formulation comprising:

a)

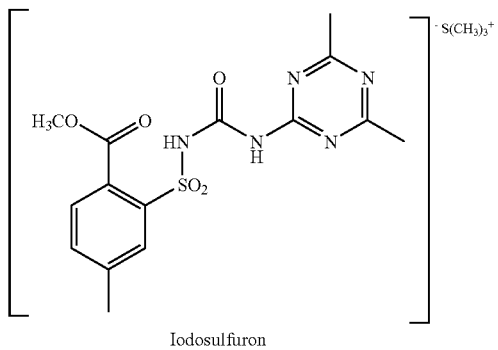

Iodosulfuron b) customary auxiliaries and additives.

22. A formulation comprising:

a) at least one sulfonylurea salt of the formula (Ia):

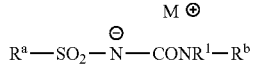
(1a)

wherein $R^1$ is H or $C_1$–$C_{10}$-hydrocarbon radical, $R^a$ is a radical of the formula (IVa) or (IVb):

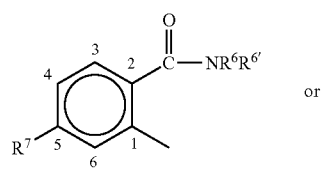
IVa or

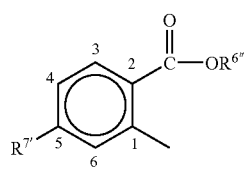
IVb $R^4$ is halogen, a substituted or unsubstituted $C_1$–$C_{20}$-hydrocarbon radical or $C_1$–$C_{20}$-hydrocarbonoxy radical, $R^5$ is H, halogen, or a substituted or unsubstituted $C_1$–$C_{20}$-hydrocarbon radical or $C_1$–$C_{20}$-hydrocarbonoxy radical, which may be substituted by one or more radicals from the group consisting of halogen and ($C_1$–$C_3$)-alkoxy, or ($C_1$–$C_5$)-alkoxy which may be substituted by one or more radicals from the group consisting of halogen and ($C_1$–$C_3$)-alkoxy, $R^6$ and $R^{6'}$ are identical or different and are H or a substituted or unsubstituted $C_1$–$C_{20}$-hydrocarbon radical, where $R^6$ and $R^{6'}$ may form an unsubstituted or substituted ring, $R^7$ is H, halogen, OH, $NR^xR^y$, in which $R^x$ and $R^y$ are H or ($C_1$–$C_3$)-alkyl, or $R^7$ is N—($C_1$–$C_3$)-alkyl-N-acylamino or N-acylamino or a substituted or unsubstituted $C_1$–$C_{20}$-hydrocarbon radical or hydrocarbonoxy radical, $R^{6''}$ is a substituted or unsubstituted $C_1$–$C_{20}$-hydrocarbon radical, $R^{7'}$ is H, halogen, OH, $NR^xR^y$, in which $R^x$ and $R^y$ are H or ($C_1$–$C_3$)-alkyl, or $R^{7'}$ is N—($C_1$–$C_3$)-alkyl-N-acylamino, N-acylamino or a substituted or unsubstituted $C_1$–$C_{20}$-hydrocarbon radical or a $C_1$–$C_{20}$-hydrocarbonoxy radical, $M^+$ is sulfonium ion $R^b$ is a radical of the formula:

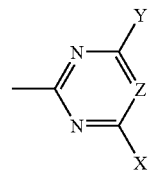

wherein

X is substituted or unsubstituted ($C_1$–$C_6$)-alkyl, substituted or unsubstituted ($C_1$–$C_6$)-alkoxy, halogen, substituted or unsubstituted ($C_1$–$C_6$)-mercaptoalkyl or ($C_1$–$C_3$)-mono- or ($C_1$–$C_3$)-dialkylamino, Y is substituted or unsubstituted ($C_1$–$C_6$)-alkyl, substituted or unsubstituted ($C_1$–$C_6$)-alkoxy, halogen, substituted or unsubstituted ($C_1$–$C_6$)-mercaptoalkyl or ($C_1$–$C_3$)-mono- or ($C_1$–$C_3$)-dialkylamino, and Z is N, b) customary auxiliaries and additives.

23. A formulation comprising:

a) at least one sulfonylurea salt of the formula (Ia):

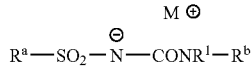
(1a)

wherein $R^1$ is H or $C_1$–$C_{10}$-hydrocarbon radical, $R^a$ is a radical of the formula (IVa) or (IVb):

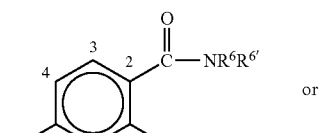

IVa or

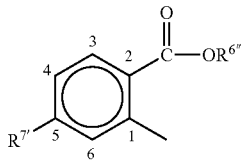

IVb $R^4$ is halogen, a substituted or unsubstituted $C_1$–$C_{20}$-hydrocarbon radical or $C_1$–$C_{20}$-hydrocarbonoxy radical, $R^5$ is H, halogen, or a substituted or unsubstituted $C_1$–$C_{20}$-hydrocarbon radical or $C_1$–$C_{20}$-hydrocarbonoxy radical, which may be substituted by one or more radicals from the group consisting of halogen and ($C_1$–$C_3$)-alkoxy, or ($C_1$–$C_5$)-alkoxy which may be substituted by one or more radicals from the group consisting of halogen and ($C_1$–$C_3$)-alkoxy, $R^6$ and $R^{6'}$ are identical or different and are H or a substituted or unsubstituted $C_1$–$C_{20}$-hydrocarbon radical, where $R^6$ and $R^{6'}$ may form an unsubstituted or substituted ring, $R^7$ is H, halogen, OH, $NR^xR^y$, in which $R^x$ and $R^y$ are H or ($C_1$–$C_3$)-alkyl, or $R^7$ is N—($C_1$–$C_3$)-alkyl-N-acylamino or N-acylamino or a substituted or unsubstituted $C_1$–$C_{20}$-hydrocarbon radical or hydrocarbonoxy radical, $R^{6''}$ is a substituted or unsubstituted $C_1$–$C_{20}$-hydrocarbon radical, $R^{7'}$ is H, halogen, OH, $NR^xR^y$, in which $R^x$ and $R^y$ are H or ($C_1$–$C_3$)-alkyl, or $R^{7'}$ is N—($C_1$–$C_3$)-alkyl-N-acylamino, N-acylamino or a substituted or unsubstituted $C_1$–$C_{20}$-hydrocarbon radical or a $C_1$–$C_{20}$-hydrocarbonoxy radical, $M^+$ is tertiary sulfonium ion, $R^b$ is a radical of the formula:

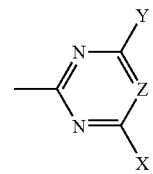

wherein

X is substituted or unsubstituted ($C_1$–$C_6$)-alkyl, substituted or unsubstituted ($C_1$–$C_6$)-alkoxy, halogen, substituted or unsubstituted ($C_1$–$C_6$)-mercaptoalkyl or ($C_1$–$C_3$)-mono- or ($C_1$–$C_3$)-dialkylamino, Y is substituted or unsubstituted ($C_1$–$C_6$)-alkyl, substituted or unsubstituted ($C_1$–$C_6$)-alkoxy, halogen, substituted or unsubstituted ($C_1$–$C_6$)-mercaptoalkyl or ($C_1$–$C_3$)-mono- or ($C_1$–$C_3$)-dialkylamino, and Z is N, b) customary auxiliaries and additives.

24. The formulation of claim 23, wherein $M^+$ is triphenyl $S^+$ or tri($C_1$–$C_{30}$)alkyl $S^+$.

25. The formulation of claim 24, wherein $M^+$ is trimethyl $S^+$.

* * * * *